United States Patent [19]
McDonald

[11] Patent Number: 6,138,307
[45] Date of Patent: Oct. 31, 2000

[54] CORNEAL INTRA-STROMEL PROSTHESES

[75] Inventor: Henry H. McDonald, Rancho Mirage, Calif.

[73] Assignee: Surgical Concepts, Inc., Newport Beach, Calif.

[21] Appl. No.: 09/306,845

[22] Filed: May 6, 1999

[51] Int. Cl.$^7$ ........................................ A61F 2/14
[52] U.S. Cl. ........................................ 6/5.11; 6/4.1
[58] Field of Search .................. 623/5, 4, 5.11, 623/4.1; 606/4, 5; 128/898

[56] References Cited

U.S. PATENT DOCUMENTS

| | | | |
|---|---|---|---|
| 5,405,384 | 4/1995 | Silverstrini | 623/5 |
| 5,722,971 | 3/1998 | Peyman | 606/5 |
| 5,944,752 | 8/1999 | Silvestrini | 623/5 |

*Primary Examiner*—Dinh X. Nguyen
*Attorney, Agent, or Firm*—William W. Haefliger

[57] ABSTRACT

In the method of distorting at least one of the anterior and posterior surfaces of the cornea so as to alter the dioptric power of the cornea to favorably alter the refraction of light rays so as to enhance image clarity, the steps include effecting multiple cuts near the corneal limbus, outwardly of the central part of the cornea; providing multiple inert prostheses having tapered wedge configurations; and inserting the prostheses into cuts in wedging directions.

31 Claims, 4 Drawing Sheets

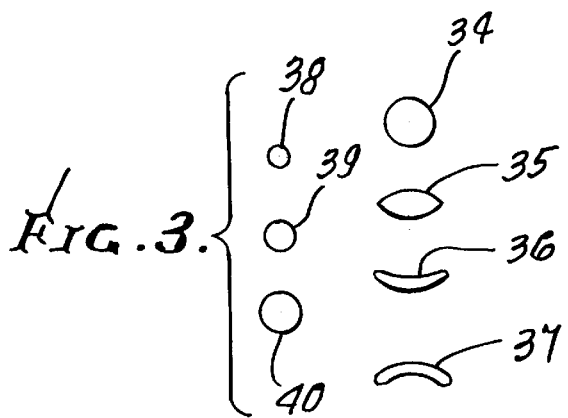
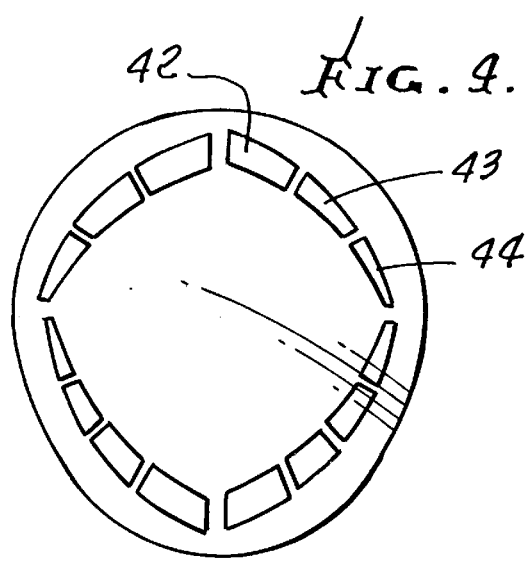
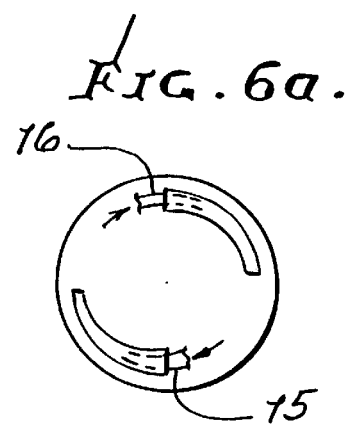
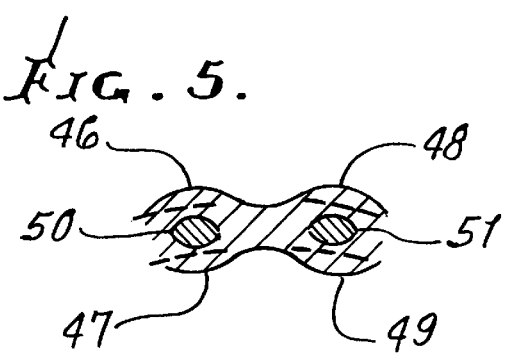
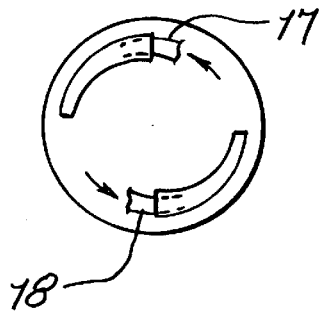

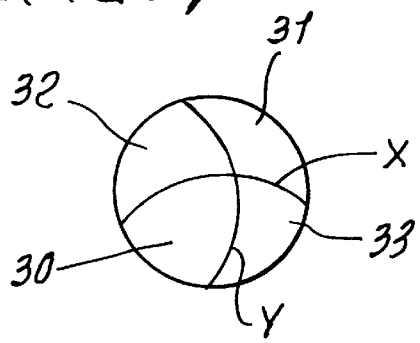
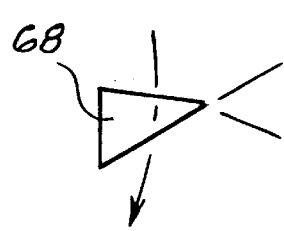
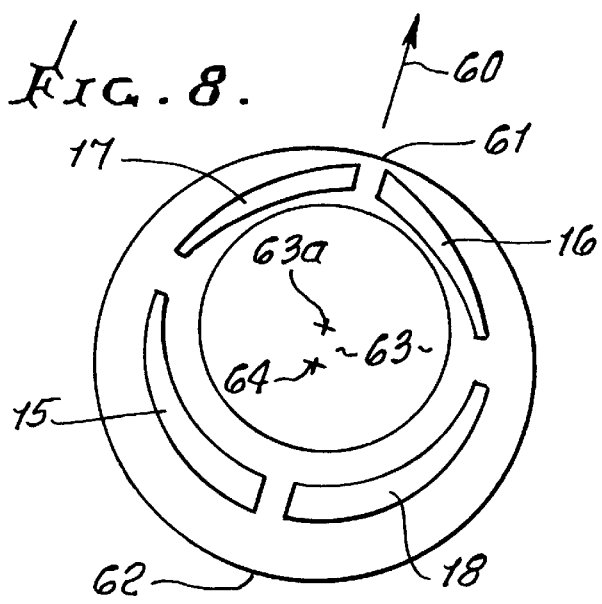
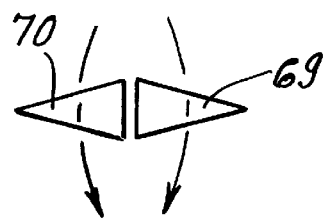
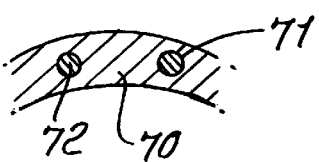
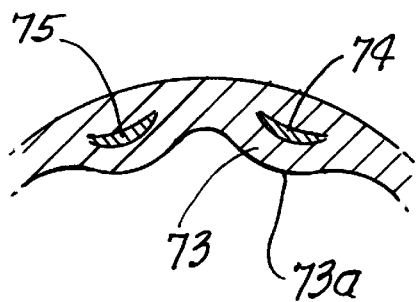
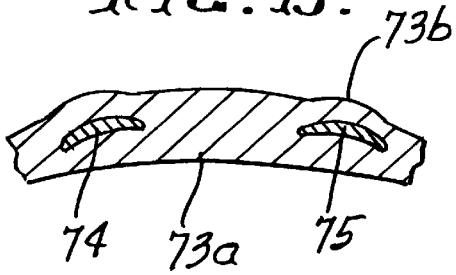

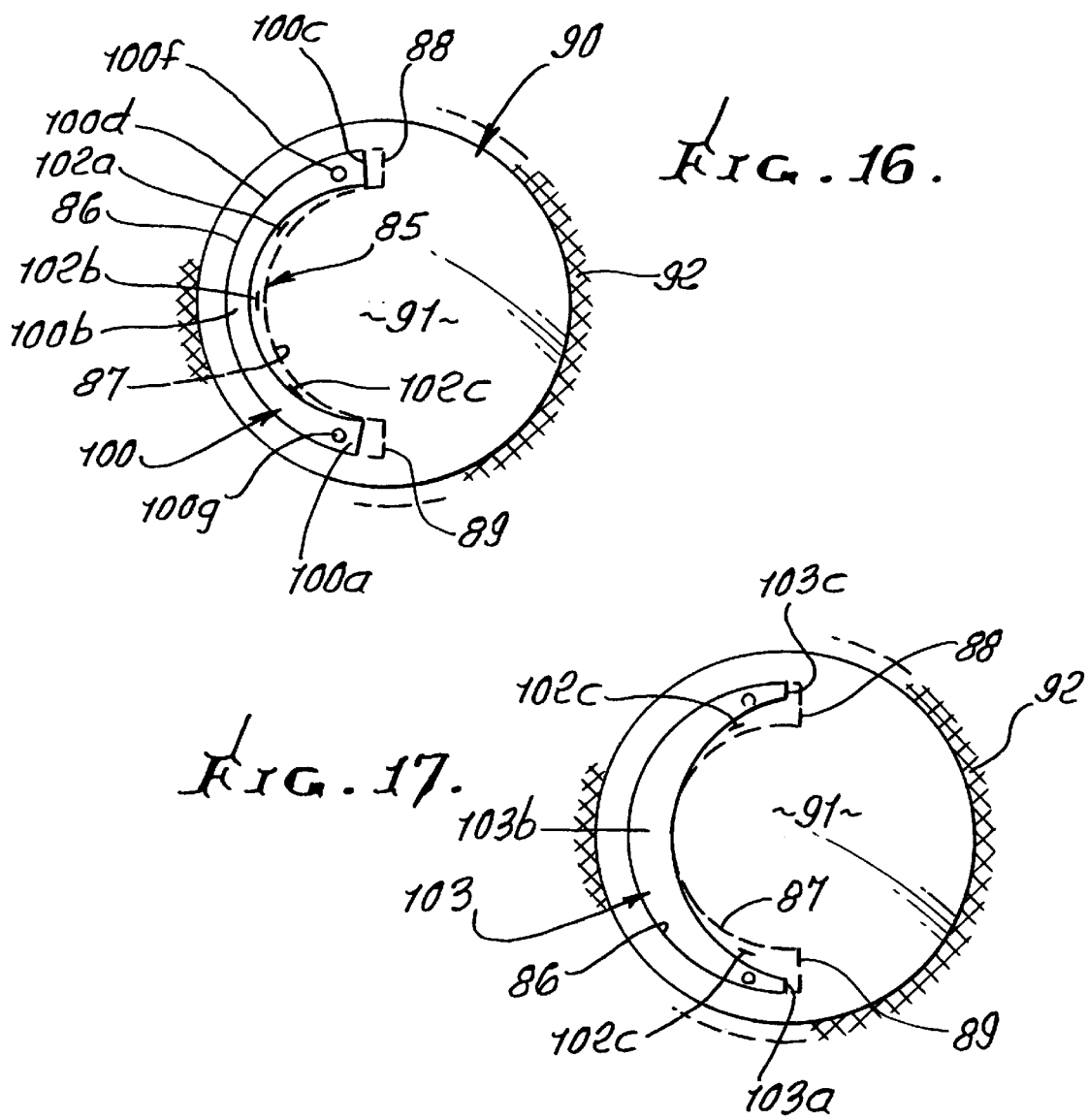

CORNEAL INTRA-STROMEL PROSTHESES

BACKGROUND OF THE INVENTION

This invention relates generally to altering the dioptric power of corneal surfaces of the eye; more particularly it concerns insertion of multiple inert, intra-stroma, prostheses into cuts formed in outer portions of the cornea, to assist in neutralization of myopia, hyperopia, and correction of astigmatic conditions.

A nearsighted person, to see clearly at a distance, requires a convex plus power to focus the rays more forward to the macula. The opposite condition exists for the far-sighted individual who requires the distortion of the cornea to bend the rays of light closer to the macula posteriorly.

With the intra-stroma insertion into the cornea of a circular plastic mass, a bulging distortion of the anterior and/or posterior surfaces of the cornea can be produced, which can change the diopter power of the cornea, to favorably enhance the bending of rays of light to focus on the macula and create a clear image.

While efforts have been made to effect controlled bulging of the cornea, difficulties have been encountered in achieving corrections greater than 3.5 diopters of myopia, and to achieve the same status for hyperoptic corrections; and difficulties have been encountered in achieving refractively corrected astigmatism and prismatic distortions. There is continuing need for improvements in effecting controlled bulging of the cornea, in such manner as to achieve the desired corrections for astigmatism and for prismatic distortions.

SUMMARY OF THE INVENTION

It is a major object of the invention to provide solutions to the above referenced problems and to meet the stated need.

Basically, the invention provides a method of distorting the anterior and/or posterior surfaces of the cornea so as to alter the dioptric power of the cornea to favorably alter the refraction of light rays so as to enhance image clarity, the steps that include a) effecting multiple cuts near the corneal limbus, outwardly of the central part of the cornea, b) providing multiple inert prostheses having tapered wedge configurations, c) and inserting said prostheses into the cuts in wedging directions.

As will be seen, the prostheses may have arc configuration in the direction of taper to correspond substantially to corneal curvature, whereby multiple of such prostheses may be located in the cornea outer extent, to taper in directions extending about the central pupil zone of the cornea.

It is another object of the invention to provide four of such prostheses inserted into four cuts respectively in the corneal stroma. In the case of astigmatism, the four tapered prostheses are inserted with their narrowest ends inserted first, and into four quandrants of the stroma, the resultant bulging of the cornea producing two perpendicular dioptric values to neutralize the two different refractive axes of an astigmatic distortion in vision.

Preservation of the clarity of the cornea in the middle of the pupillary stroma is maintained without scarring because the inert prostheses do not contact this particular area of the cornea. The prosthetic devices may be recoverable, and in contrast to correctional radial and laser keratotomies, in which tissue is irreparably destroyed. A replacement for changes in corneal refraction is thereby made possible, and clear, central corneal tissue is maintained.

Another object is to provide at least one prosthesis having arcing taper in one direction about the central part of the cornea, and at least another of said prostheses being provided to have arcing taper in the opposite direction about the central part of the cornea.

A further object is to provide first and second of the prostheses inserted to have arcing taper in one direction about the central part of the cornea, and third and fourth of such prostheses are provided and inserted to have arcing taper in the opposite direction about the central part of the cornea. In this regard, the prostheses are preferably inserted and positioned to have the following circular position sequence in the cornea:

first prosthesis third prosthesis second prosthesis fourth prosthesis

An additional object is to effect insertion to enable easy recovery of the prostheses from the cornea, and including recovering at least one of the prostheses from the cornea and inserting a replacement prosthesis of different configuration into the cornea. The invention makes possible the selective replacement of at least two of said prostheses with prostheses of different dimensional configurations, for enhancing desired dioptric correction.

These and other objects and advantages of the invention, as well as the details of an illustrative embodiment, will be more fully understood from the following specification and drawings, in which:

DRAWING DESCRIPTION

FIG. 3 is a section taken through prostheses of different cross-sections, like cross-section 1a;

FIG. 4 is a view like FIG. 1, but showing a large number of tapering prostheses inserted along a loop in the cornea;

FIG. 5 is a section taken through the cornea in which a prostheses has been inserted, and showing controlled bulging of anterior and posterior surfaces;

FIGS. 6a and 6b are frontal views of a cornea showing a two step slit formation process, the slits to receive prostheses;

FIG. 7 is a perspective view of a domed surface, representative of a corneal convex surface, with four quadrants delineated;

FIG. 8 is a view like FIG. 1, but showing shifting of the four prostheses locations to effect lateral shifting of the pupil;

FIG. 9 is a view of a prism to show its effect in corresponding prosthesis creation of a corneal prismatic effect;

FIG. 10 is a view like FIG. 9 to show creation of a corneal prismatic effect to decrease phoria or phorias and/or diplopia, even simultaneously with astigmatic intra-stromel correction;

FIG. 11 is a section showing bulging of opposite surfaces of a cornea;

FIGS. 12 and 13 are sections through corneas with prostheses creating various surface bulges;

FIGS. 14 and 15 are views like FIG. 1 showing further modifications;

FIGS. 16 and 17 are views showing a single prosthesis inserted into a cornea; and FIG. 18 is a section showing controlled corneal surface bulging to vary light refraction.

DETAILED DESCRIPTION

Figure 1:
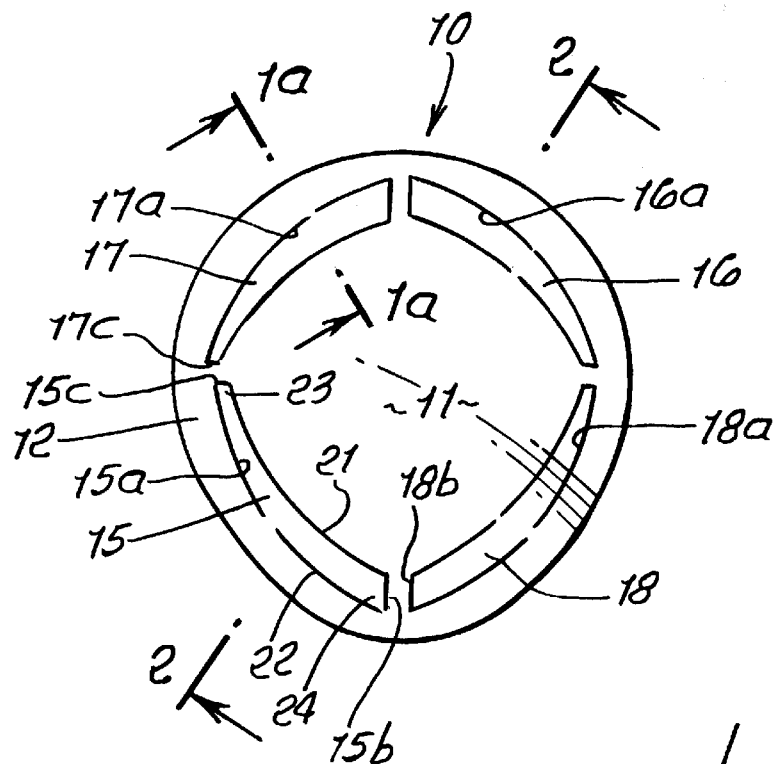
FIG. 1 is a frontal view of the cornea, with four prostheses in inserted condition.
Figure 2:
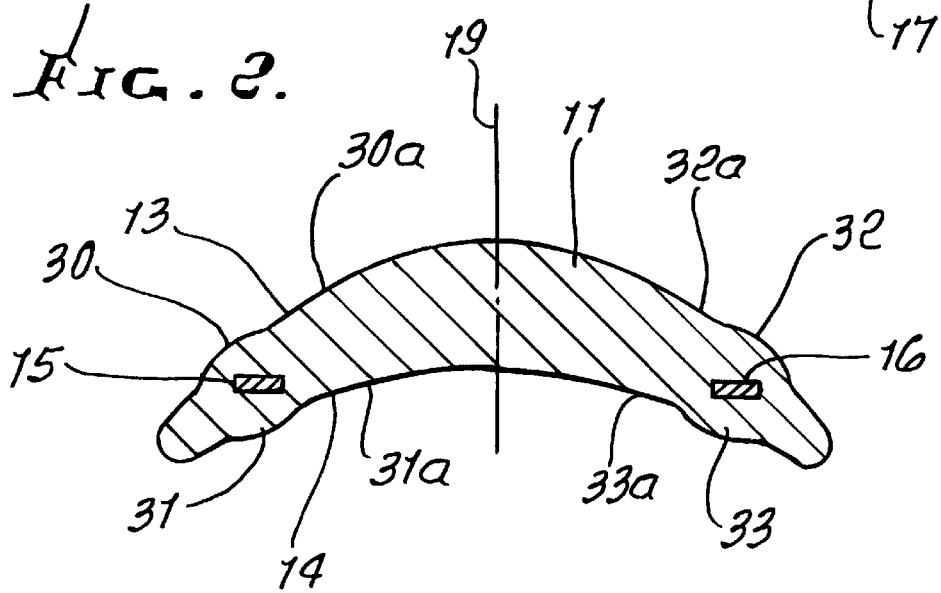
FIG. 2 is an axial section taken through a cornea, showing locations of typical slits formed in the corneal limbus.

Referring first to FIGS. 1 and 2, a human cornea 10 has an inner zone 11, i.e. the pupil area, and an outer annular zone 12, the limbus area. Inert prostheses are provided in outer zone 12 for distorting the anterior and posterior surfaces 13 and 14 of the cornea, and particularly the limbus, which then affects the zone 12, so as to alter the dioptric power of the cornea to favorably alter the refraction of light rays so as to enhance image clarity at the retina.

Four prostheses 15–18 are provided and are inserted into four corresponding cuts 15a–18a in outer zone 12, as shown. Such cuts are made to extend about the corneal axis 19, in a generally circular direction. The elongated prostheses may be alike, and have tapered wedge configuration along their arc lengths. Each prosthesis, such as 15, has inner and outer walls 21 and 22 which are differentially arc shaped, the two arcs tapering toward one another and toward the terminal end 23. The opposite end 24 is widest.

The directions of prosthesis taper are organized as follows:

15 and 16 clockwise

17 and 18 counterclockwise.

Accordingly, the first and second of said prostheses are provided and inserted to have arcing taper in one direction about the central part of the cornea, and third and fourth of said prostheses are provided and inserted to have arcing taper in the opposite direction about the central part of the cornea. Such prostheses are inserted to have the following circular position sequence in the cornea:

first prosthesis third prosthesis second prosthesis fourth prosthesis.

See also FIG. 6a showing step 1 insertion of 15 and 16; and FIG. 6b showing step 2 insertion of 17 and 18. The cuts to receive the prostheses may be effected by a similar two-step procedure. The four quandrants of the cornea, affected by bulging created by prostheses insertion, are indicated at 30–33 in FIG. 7. Minimum bulging is associated with axial plane X, toward which the prostheses 15 and 17 taper and toward which prostheses 16 and 18 also taper (see FIG. 1); and maximum bulging is associated with axial plane Y, near which the prostheses have their widest ends (ends with maximum cross-sections, for example ends 15b and 18b). The prostheses have their minimum cross-sections at their narrowest ends (for example ends 15c and 17c). Since the prostheses are tapered, endwise, their endwise insertion in the direction of taper is facilitated, and their endwise withdrawal in the opposite direction is also facilitated. Prostheses of different sizes (lengths and cross-sections) can therefore be successively inserted and withdrawn, until the patient's vision is maximally clarified. After final prostheses insertion, retention sutures can be formed in the cornea at the widest ends of the cuts.

FIG. 2 shows bulging of the cornea at posterior and anterior regions 30 and 31, and also at 32 and 33, near the inserted prostheses, which also affects curvatures at the pupillary surfaces 30a–33a. The prostheses may consist of transparent or light transmitting plastic material, or of COLLAMER, a synthetic, inert, light-passing material manufactured by Staar AG of Switzerland.

FIG. 3 shows differing cross-sections of various prostheses, as at 34–40. FIG. 4 shows prostheses of shorter tapered lengths, as at 42–44, at each quandrant, the overall tapering organization of the segmented prostheses being consistent with those shown in FIG. 1. FIG. 5 also shows bulge zones 46–49 of the cornea created by insertion of generally looping cross-section (outwardly convex) prostheses 50 and 51.

FIG. 8 shows prostheses 15–18 like those of FIG. 1, and arranged in the same pattern; however, they are eccentrically shifted in direction 60 toward corneal edge 61, and away from edge 62. Therefore, the created bulging effects a slight shifting of the pupil zone 63 toward edge 61, as shown. The shifted pupil center is seen at 63a, and the center or axis of the cornea appears at 64.

FIGS. 9 and 10 show prisms 68–70 serving to refract light rays as shown, and illustrative of corneal bulging to create different refraction effects.

FIG. 11 shows a corneal zone 70 mildly outwardly bulged by smaller cross-section prostheses 71 and 72; FIG. 12 shows corneal zone 73 preferentially outwardly bulges at posterior surface 73a, by circular segment shaped prostheses cross-sections 74 and 75; and FIG. 13 shows corneal zone 73 preferentially bulged at anterior surface 73b by circular segment shaped prostheses 74 and 75. The posterior surface is here flattened at 73a.

In FIG. 1, the widest ends of successive prostheses can extend adjacent one another, or can be at least partially joined, as seen in FIGS. 14 and 15. In each view, each of the two prostheses has opposite ends and the effective singular prosthesis tapers toward each of said ends, whereby the prosthesis is provided to have crescent shape.

The invention also extends to the method of distorting at least one of the anterior and posterior surfaces of the cornea so as to alter the dioptric power of the cornea to favorable alter the refraction of light rays so as to enhance image clarity, the steps that include a) effecting at least one cut in the cornea outwardly of the central part of the cornea, b) providing at least one inert prosthesis having variable width configuration, c) and inserting said prosthesis into said cut to be retained therein and to effect said distorting.

Figure 1A:
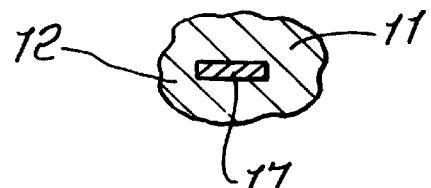
FIG. 1a is a section taken on lines 1a—1a of FIG. 1.

In the example of FIG. 16, an arc shaped slit or cut 85 is formed edgewise or sidewardly in the cornea 90 along arc shaped outer edge 86, arc shaped inner edge (see broken line) 87, end 88 and end 89 (shown by broken lines). The slit or cut is formed outwardly of the central (pupil) portion 91 of the cornea, and near but not in the corneal limbus (zone 92). A single prosthesis 100 is introduced into the slit, and has a cross-section like that seen in FIG. 1a, but that cross-section varies in generally radial width along the arch-shaped length. In FIG. 16 the prosthesis tapers along its length, and in a clockwise direction the width decreases between end 100a and mid-portion 100b, and then increases in width between 100b and 100c. The curvature of outer edge 100d conforms generally to that of slit edge 86; and curvature of inner edge 100c of the prosthesis is greater than that of slit edge 87. Local indentations or protrusions may be provided as at 100f and 100g, in or on the prosthesis to enable assured grasping by an instrument that inserts or withdraws the prosthesis; and sutures may be made as at 102a, b, and c to at least partly close the slit at its radially inner side, preventing wiggle or unwanted displacement of the prosthesis. Numeral 100e designates the narrowed region of the prosthesis.

FIG. 17 shows a similar arrangement, except that the arc shaped prosthesis 103 increases in width from end 103a to mid portion 103b, and then decreases in width from 103b and end 103c.

The prosthesis or prostheses of the invention are inserted into a cut or cuts in the cornea to effect at least one of the following:

i) increased or decreased bulging of at least one of the anterior and posterior surfaces of the cornea, ii) increased or decreased bulging of both of the anterior and posterior surfaces of the cornea, iii) controlled reduction in curvature at the convex posterior surface of the cornea.

FIG. 18 schematically shows in section how a prosthesis 106 or prostheses 106a and 106b effect reduction in curvature of the posterior side of the cornea, as by deformation (bulging) from the solid line curvature 107 to the broken line curvature 108 which affects the overall curvature in a plane corresponding to the plane of FIG. 18. That same or similar selective bulging can be produced in a plane normal to the plane of FIG. 18, to remedy astigmatism, for example. Controlled corneal surface refraction of light is enabled. This procedure avoids risk of rupture of the cornea as is possible when laser treatment is employed, and can be reversed, as by removal of the prosthesis or prostheses (reversal not being possible with laser treatment).

I claim:

1. In the method of distorting at least one of the anterior and posterior surfaces of the cornea so as to alter the dioptric power of the cornea to favorably alter the refraction of light rays so as to enhance image clarity, the steps that include a) effecting multiple cuts near the corneal limbus, outwardly of the central part of the cornea, b) providing multiple inert prostheses each having endwise taper to form a wedge, c) and inserting said prostheses into said cuts in wedging directions.

2. The method of claim 1 wherein said prostheses are provided to have arc configuration in the direction of taper to correspond substantially to corneal curvature, said cuts formed between the pupil and the limbus.

3. The method of claim 2 wherein four of said prostheses are inserted into four cuts, respectively, in the cornea.

4. The method of claim 1 wherein the cornea has an axis, and said cuts are effected to extend about said axis.

5. The method of claim 2 wherein at least one of said prostheses is provided to have arcing taper in one direction about the central part of the cornea, and whereas at least another of said prostheses is provided to have arcing taper in the opposite direction about the central part of the cornea.

6. The method of claim 2 wherein a first and second of said prostheses are provided and inserted to have arcing taper in one direction about the central part of the cornea, and a third and fourth of said prostheses are provided and inserted to have arcing taper in the opposite direction about the central part of the cornea.

7. The method of claim 6 wherein said prostheses are inserted to have the following circular position sequence in the cornea:

first prosthesis
   third prosthesis
   second prosthesis
   fourth prosthesis.

8. The method of claim 6 wherein said prostheses are inserted to have relatively narrow ends of the first and third prostheses in proximity to one another, and to have the relatively narrowed ends of the second and fourth prostheses in proximity to one another.

9. The method of claim 1 wherein said inserting is effected to enable easy recovery of the prostheses from the cornea, and including recovering at least one of said prostheses from the cornea and inserting a replacement prosthesis of different configuration into the cornea.

10. The method of claim 3 including selectively replacing at least two of said prostheses with prostheses of different dimensional configurations.

11. The method of claim 1 wherein there are at least two of said prostheses which are provided in the corneal limbus.

12. The method of claim 11 wherein each of said two prostheses has opposite ends and the prosthesis tapers toward each of said ends, whereby the prosthesis is provided to have crescent shape.

13. The method of claim 1 involving providing suturing in the cornea to block endwise withdrawal of the prostheses from said cuts.

14. The method of claim 3 including providing suturing in the cornea to block excessive movement of the prostheses in the cuts.

15. For use in a cornea, wherein multiple cuts are formed near the corneal limbus, outwardly of the central part of the cornea, the combination comprising a) multiple inert prostheses in a cluster, each prothesis having endwise taper to form a wedge, b) said prostheses insertible into said cuts in corneal wedging directions, c) whereby the anterior and posterior surfaces of the cornea may be distorted to alter the dioptric power of the cornea for favorably altering the separation of light rays to enhance perceived image clarity.

16. The combination of claim 15 wherein said prostheses have arc configuration in the direction of taper to correspond substantially to corneal curvature.

17. The combination of claim 16 wherein said prostheses include four prostheses insertible into four cuts, respectively, in the cornea.

18. The combination of claim 15 wherein the prostheses extend about an axis corresponding to the axis of the cornea.

19. The combination of claim 18 wherein at least one of said prostheses has arcing taper in one direction about said axis, and at least another of said prostheses has arcing taper in the opposite direction about said axis.

20. The combination of claim 16 wherein first and second of said prostheses have arcing taper to extend in one direction about the central part of the cornea, and a third and fourth of said prostheses have arcing taper to extend in the opposite direction about the central part of the cornea.

21. The combination of claim 20 wherein the prostheses have the following circular position sequence for insertion in the cornea:

first prosthesis
   third prosthesis
   second prosthesis
   fourth prosthesis.

22. The combination of claim 20 wherein the first and third prostheses have relatively narrow ends in proximity to one another, and the second and fourth prostheses have relatively narrow ends in proximity to one another.

23. The combination of claim 15 wherein at least one of said prostheses is a replacement prosthesis to be inserted in a cut after removal of a prior inserted prosthesis.

24. In the method of distorting at least one of the anterior and posterior surfaces of the cornea so as to alter the dioptric power of the cornea to favorable alter the refraction of light rays so as to enhance image clarity, the steps that include a) effecting at least one cut in the cornea outwardly of the central part of the cornea, b) providing at least one inert prosthesis having variable width configuration, c) and inserting said prosthesis into said cut to be retained therein and to effect said distorting, and so as to extend only part-way about said central part of the cornea, d) and wherein said at least one prosthesis is or are provided to have arc configuration in a direction of taper that corresponds substantially to corneal curvature, said at least one cut formed between the pupil and the limbus.

25. The method of claim 24 wherein said multiple prostheses are inserted into multiple cuts formed to he spaced about the central part of the cornea, and including the step of adjusting the position or positions of at least one of said prostheses relative to other previously inserted prostheses to enhance clarity of vision.

26. In the method of distorting at least one of the anterior and posterior surfaces of the cornea so as to alter the dioptric power of the cornea to favorable alter the refraction of light rays so as to enhance image clarity, the steps that include a) effecting multiple separate cuts in the cornea outwardly of the central part of the cornea, b) providing multiple prostheses having variable width configurations along their lengths, c) and successive inserting said prostheses into said respective separate cuts to be retained therein and to effect said distorting.

27. The method of claim 26 wherein said variable width configuration defines one of the following:

i) prosthesis width that decreases and then increases along arc shaped length of the prosthesis, ii) prosthesis width that increases and then decreases along arc shaped length of the prosthesis.

28. The method of claim 26 wherein said prosthesis is inserted into the cut to effect one of the following:

i) increased or decreased bulging of at least one of the anterior and posterior surfaces of the cornea, ii) increased or decreased bulging of both of the anterior and posterior surfaces of the cornea, iii) controlled reduction in curvature a at the convex posterior surface of the cornea.

29. The method of claim 26 including suturing the cut to retain the prosthesis therein against unwanted in-place displacement.

30. The method of claim 26 including suturing the cornea near the cut to assist in in-place retention of the prosthesis or prostheses.

31. The method of claim 26 including providing a deformation or deformations at the surface of the prosthesis or prostheses to facilitate instrument grasping of the prosthesis or prostheses.

* * * * *